(12) United States Patent
Shibaguchi et al.

(10) Patent No.: US 9,764,029 B2
(45) Date of Patent: Sep. 19, 2017

(54) TUMOR PROLIFERATION INHIBITOR CONTAINING ULTRASOUND-SENSITIVE SUBSTANCE AND METHOD FOR INHIBITING TUMOR PROLIFERATION BY USING TUMOR PROLIFERATION INHIBITOR AND LOW-INTENSITY PULSED ULTRASOUND WAVES

(71) Applicant: Fukuoka University, Fukuoka-shi, Fukuoka (JP)

(72) Inventors: Hirotomo Shibaguchi, Fukuoka (JP); Hirofumi Tsuru, Fukuoka (JP)

(73) Assignee: FUKUOKA UNIVERSITY, Fukuoka-Shi (JP)

(*) Notice: Subject to any disclaimer, the term of this patent is extended or adjusted under 35 U.S.C. 154(b) by 0 days.

(21) Appl. No.: 14/186,859

(22) Filed: Feb. 21, 2014

(65) Prior Publication Data
US 2014/0287000 A1 Sep. 25, 2014

Related U.S. Application Data

(62) Division of application No. 13/812,922, filed as application No. PCT/JP2011/069590 on Aug. 30, 2011, now abandoned.

(30) Foreign Application Priority Data

Aug. 30, 2010 (JP) .................................. 2010-192916

(51) Int. Cl.
| | | |
|---|---|---|
| *A61K 41/00* | (2006.01) | |
| *A61K 31/409* | (2006.01) | |
| *A61K 31/7135* | (2006.01) | |

(52) U.S. Cl.
CPC ........ *A61K 41/0047* (2013.01); *A61K 31/409* (2013.01); *A61K 31/7135* (2013.01); *A61K 41/0033* (2013.01)

(58) Field of Classification Search
CPC .............. A61K 41/0047; A61K 31/409; A61K 31/7135; A61K 41/0033

USPC .......................................................... 424/400
See application file for complete search history.

(56) References Cited

PUBLICATIONS

Hachimine et al., "Sonodynamic therapy of cancer using a novel porphyrin derivative, DCPH-P-Na(I), which is devoid of photosensitivity", Cancer Sci., vol. 98, No. 6, pp. 916-920, Jun. 2007.
International Search Report, issued in PCT/JP2011/069590, dated Oct. 25, 2011.
Iwase et al., "Induction of Apoptosis by Sonochemical Activation of Novel Porphyrin Derivative, DCPH-P-Na(I)" Ouyouyakuri, vol. 78, No. 5/6, p. 45, Aug. 13, 2010.
Kinoshita et al., "Mechanism of Porphyrin-Induced Sonodynamic Effect: Possible Role of Hyperthermia", Radiation Research, vol. 165, pp. 299-306 (2006).
Miyoshi et al., "Effect of Gallium-Porphyrin Analogue ATX-70 on Nitroxide Formation from a Cyclic Secondary Amine by Ultrasound: On the Mechanism of Sonodynamic Activation", Radiation Research, vol. 143, pp. 194-202 (1995).
Tsuru et al., "Anticancer effect of sonodynamic therapy with a novel porphyrin derivative, DEG-Mn-DP-H", Japanese Journal of Medical Ultrasonics, vol. 37, Suppl. S468, 83-AP-001, Apr. 15, 2010.
Yanagisawa et al., "Phagocytosis of Ultrasound Contrast Agent Microbubbles by Kupffer Cells", Ultrasound in Med. & Biol., 2007, vol. 33, No. 2, pp. 318-325.
Yumita et al., "Hematoporphyrin as a Sensitizer of Cell-damaging Effect of Ultrasound", Jpn. J. Cancer Res. vol. 80, pp. 219-222, Mar. 1989.

*Primary Examiner* — Adam C Milligan
(74) *Attorney, Agent, or Firm* — Birch, Stewart, Kolasch & Birch, LLP

(57) ABSTRACT

Provided are a tumor proliferation inhibitor and a method for inhibiting tumor proliferation both of which can be applied to a minimally invasive cancer treatment using low-intensity pulsed ultrasound. The present invention provides a tumor proliferation inhibitor containing an ultrasound-sensitive substance and an acoustic cavitation phenomenon-enhancing substance, and provides a method for inhibiting tumor proliferation that can exhibit a tumor proliferation-inhibitory effect using the tumor proliferation inhibitor in combination with low-intensity pulsed ultrasound of a degree that is used in ultrasound diagnosis, and that can be applied to a minimally invasive cancer treatment using low-intensity pulsed ultrasound.

1 Claim, 4 Drawing Sheets

TUMOR PROLIFERATION INHIBITOR CONTAINING ULTRASOUND-SENSITIVE SUBSTANCE AND METHOD FOR INHIBITING TUMOR PROLIFERATION BY USING TUMOR PROLIFERATION INHIBITOR AND LOW-INTENSITY PULSED ULTRASOUND WAVES

The present application is a Divisional of and claims priority to U.S. patent application Ser. No. 13/812,922, filed Jan. 29, 2013, which is the National Stage of PCT/JP2011/069590, filed on Aug. 30, 2011, which in turn claims priority to Japanese Patent Application JP 2010-192916 filed on Aug. 30, 2010. The entire contents of the above applications are hereby expressly incorporated by reference in their entirety.

TECHNICAL FIELD

The present invention relates to a tumor proliferation inhibitor containing an ultrasound-sensitive substance and a method for inhibiting the proliferation of tumors by using the tumor proliferation inhibitor and low-intensity pulsed ultrasound waves. More particularly, the present invention relates to a tumor proliferation inhibitor containing the ultrasound-sensitive substance and an acoustic cavitation phenomenon-enhancing substance, a tumor proliferation inhibiting method for inhibiting the tumor proliferation by activating the tumor proliferation inhibitor by low-intensity pulsed ultrasound waves, and a cancer therapy by using the ultrasound-sensitive substance and the acoustic cavitation phenomenon-enhancing substance in combination with the low-intensity pulsed ultrasound waves.

BACKGROUND TECHNOLOGY

Three major therapies for cancer treatment may include surgical therapy, chemical therapy and radiation therapy. These therapies may achieve high therapeutic results, however, they may encounter with difficulties some times because the surgical therapy is invasive or they may often force to interrupt the treatment due to strong side effects caused by the therapies. It is highly desired, accordingly, to apply low-intensity pulsed ultrasound waves as applied to ultrasound diagnosis when taken cancer treatment into consideration from a non-invasive point of view. Therefore, by applying the fact that photosensitive substances such as Photofrin is activated by an acoustic cavitation phenomenon to be caused by ultrasound waves, such photosensitive substances together with low-intensity pulsed ultrasound waves have been applied particularly to non-invasive treatments of cancers (see, for example, patent literature documents Nos. 1 and 2). It is pointed out, however, that photodynamic therapy using such photosensitive substances causes the problems that the quality of life (QOL) of patients may be impaired to a great extent by application of the photosensitive substances to patients for therapy using low-intensity pulsed ultrasound waves because the patients are forced to be isolated in a dark room for such an extended period of time as long as approximately two weeks in order to prevent the patients from side effects such as cutaneous hypersensitivity caused by a light. The use of the photosensitive substances may also cause the problem with a lower activation by ultrasound waves than by a light.

Low-intensity pulsed ultrasound waves confer the merits that they can reach the deeper portion of the living body than a light can and they are highly safe to such an extent to which they are used for echo diagnosis even for embryos. They cannot be expected, however, to demonstrate effects on treatments of cancers when they are solely applied thereto. At the present time, there has proceeded the application of the low-intensity pulsed ultrasound waves in combination with nanoparticles including, for example, nanobubbles or microbubbles to gene therapy or drug delivery system (DDS) utilizing an acoustic cavitation phenomenon to be caused by the low-intensity pulsed ultrasound waves. Problems have occurred, however, with various matters including, for instance, stability of nanoparticles in the living body when applied thereto. The combined use of the low-intensity pulsed ultrasound waves with the nanoparticles is still far away from practical use.

As described above, in order to permit the low-intensity pulsed ultrasound waves to be applied to a low invasive cancer therapy, there have to be solved many problems that may include, for example, a development of an ultrasound-sensitive substance unreactive with a light and an enhancement of effects of the ultrasound waves on a local target portion of treatment.

In order to solve the problems as described above, the present inventor has investigated the action and effects of the combined use of the low-intensity pulsed ultrasound waves with an ultrasound-sensitive substance that little reacts with a light and is activated by the ultrasound waves. As a result, it has been found that, although the combined use has exhibited a remarkably favorable effects in vitro on tumor cells (a potent cellular cytotoxicity), inhibitory effects on tumor proliferation in an in vivo experiment system using animals with cancer were not recognized to such an extent as expected from the in vitro effects although they were significant (Non-patent literature document No. 3). This implies that the ultrasound-sensitive substance is not activated by the low-intensity pulsed ultrasound waves to a sufficient extent in tumor tissues.

REFERENCES

Non-patent literature document No. 1: Yumita N., et al., Jpn. J. Cancer Res., vol. 80, pp.219-222 (1989)

Non-patent literature document No. 2: Miyoshi N., et al., Radiat. Res., vol. 143, pp.194-202 (1995)

Non-patent literature document No. 3: Hachimine, K., et al., Cancer Sci., vol. 98, no.6, pp.916-920 (2007)

SUMMARY OF INVENTION

As a result of extensive studies by the present inventor to find a method for activating an ultrasound-sensitive substance in tumor tissues for cancer therapy using low-intensity pulsed ultrasound waves, it has been found that the use of a substance capable of enhancing an acoustic cavitation phenomenon (hereinafter referred to also as "acoustic cavitation phenomenon-enhancing substance") to be induced by ultrasound waves in combination with an ultrasound-sensitive substance and low-intensity pulsed ultrasound waves upon irradiation of the ultrasound-sensitive substance with the low-intensity pulsed ultrasound waves can activate the ultrasound-sensitive substance in an in vivo experiment system using animals with cancers to achieve significantly inhibitory effects on tumor proliferation. The present invention has been completed on the basis of this finding.

Therefore, the present invention in one mode has the object to provide a tumor proliferation inhibiting agent containing an ultrasound-sensitive substance and an acoustic cavitation phenomenon-enhancing substance.

The present invention in another mode has the object to provide a method for inhibiting tumor proliferation by irradiating the tumor proliferation inhibitor and the acoustic cavitation phenomenon-enhancing substance with low-intensity pulsed ultrasound waves.

In order to achieve the above objects, the present invention in one mode provides the tumor proliferation inhibitor containing the ultrasound-sensitive substance substantially unreactive with light and the acoustic cavitation phenomenon-enhancing substance.

The present invention in a preferred embodiment provides the tumor proliferation inhibitor wherein the ultrasound-sensitive substance is a porphyrin derivative or a xanthene derivative.

The present invention in a more preferred embodiment provides the tumor proliferation inhibitor wherein the porphyrin derivative is 7,12-bis(1-(2-(2-hydroxyethoxy)ethoxy)ethyl)-3,8,13,17-tetra-methylporphyrin-2,18-dipropionato]manganese (DEG) as represented by formula [I]:

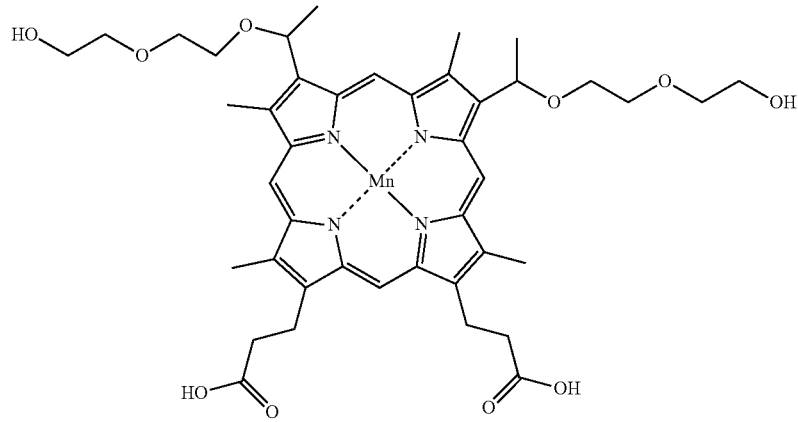

or 13,17-bis(1-carboxyethyl)-8-[2-(2,4-dichlorophenyl-hydra-zono) ethylidene]-3-ethenyl-7-hydroxy-2,7,12,18-tetramethyl-chlorin disodium salt as represented by formula [II]:

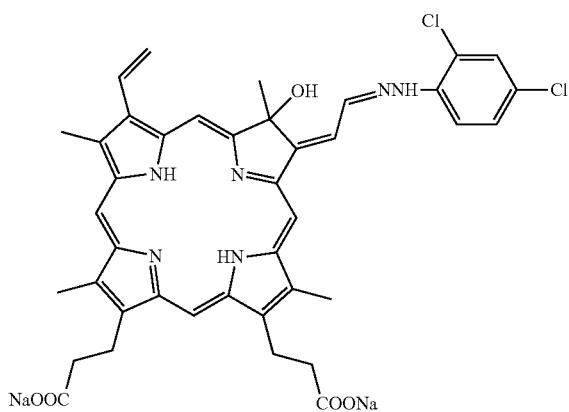

The present invention in another preferred embodiment provides the tumor proliferation inhibitor wherein the acoustic cavitation phenomenon-enhancing substance is gas-filled bubbles capable of inducing an acoustic cavitation phenomenon by low-intensity pulsed ultrasound waves, including, but being not limited to, microbubbles or nanobubbles.

The present invention in another preferred embodiment provides the tumor proliferation inhibitor wherein the acoustic cavitation phenomenon-enhancing substance is an ultrasound contrast agent containing lipid stabilized perfluorobutane microbubbles in an aqueous solution (SONAZOID™) or a microcrystalline suspension of galactose and palmitic acid which is shaken with sterile water prior to use to produce a milky suspension containing micrometer sized air bubbles (LEVOVIST™).

The present invention in another mode provides the method for inhibiting proliferation of tumors which comprises inhibiting the proliferation of tumors by irradiating the tumor proliferation inhibitor containing the ultrasound-sensitive substance and the acoustic cavitation phenomenon-enhancing substance with low-intensity pulsed ultrasound waves.

The present invention in a preferred embodiment provides the method for inhibiting the tumor proliferation wherein the ultrasound-sensitive substance is the porphyrin derivative and the xanthene derivative.

The present invention in a more preferred embodiment provides the method for inhibiting the tumor proliferation wherein the ultrasound-sensitive substance is 7,12-bis(1-(2-(2-hydroxyethoxy)-ethoxy)ethyl)-3,8,13,17-tetramethylporphyrin-2,18-dipropionato]-manganese (DEG) as represented by formula [I]:

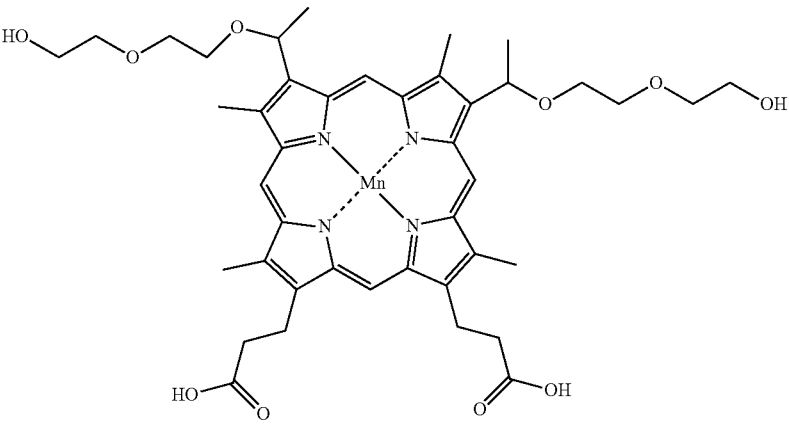

or 13,17-bis(1-carboxyethyl)-8-[2-(2,4-dichlorophenyl-hydra-zono) ethylidene]-3-ethenyl-7-hydroxy-2,7,12,18-tetramethyl-chlorin disodium salt as represented by formula [II]:

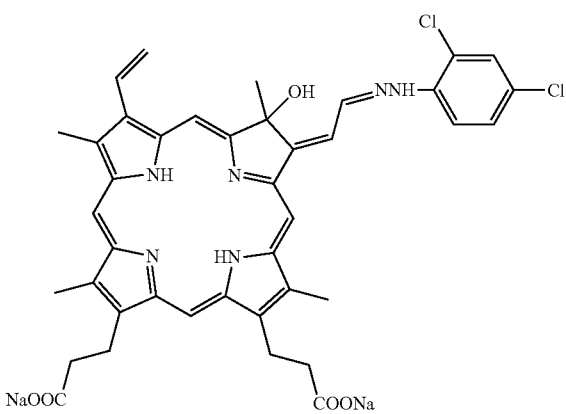

The present invention in another preferred embodiment provides the method for the inhibition of the tumor proliferation wherein the acoustic cavitation phenomenon-enhancing substance is gas-filled bubbles capable of inducing an acoustic cavitation phenomenon by ultrasound waves, including, but being not limited to, microbubbles or nanobubbles.

The present invention in another preferred embodiment provides the method for the inhibition of tumor proliferation wherein the acoustic cavitation phenomenon-enhancing substance is an ultrasound contrast agent containing lipid stabilized perfluorobutane microbubbles in an aqueous solution (SONAZOID™) or a microcrystalline suspension of galactose and palmitic acid which is shaken with sterile water prior to use to produce a milky suspension containing micrometer sized air bubbles (LEVOVIST™).

The present invention in another preferred embodiment provides the method for the inhibition of the tumor proliferation wherein the low-intensity pulsed ultrasound waves activate the acoustic cavitation phenomenon-enhancing substance and the ultrasound-sensitive substance.

EFFECTS OF THE INVENTION

The present invention provides antitumor effects on cancer therapy by activating the ultrasound-sensitive substance by the irradiation of ultrasound waves having a power as low as capable of being used for echo examination and enhancing the cytotoxic activity thereof in vivo to a remarkable extent.

BRIEF DESCRIPTION OF THE ACCOMPANYING DRAWINGS

MODES FOR CARRYING OUT THE INVENTION

Figure 1:
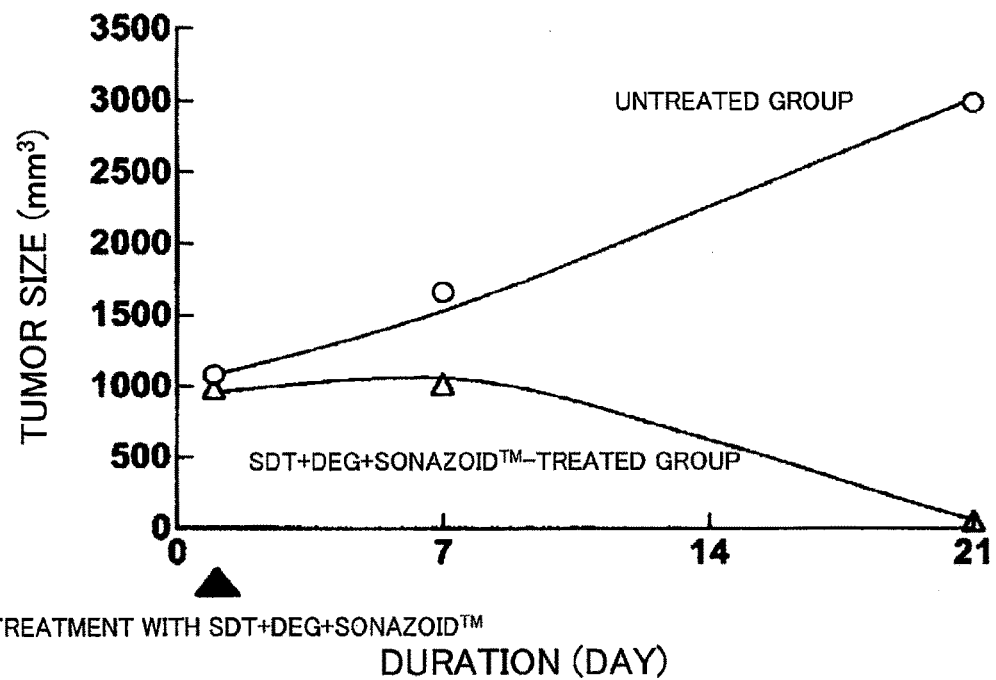
FIG. 1 is a graph showing the comparative effects of a combined administration of DEG and SONAZOID™ on tumor sizes when treated with low-intensity pulsed ultrasound waves after administration and when not treated thereafter (Example 1).

The present invention in one mode provides the tumor proliferation inhibitor containing the ultrasound-sensitive substance and the acoustic cavitation phenomenon-enhancing substance. The tumor proliferation inhibitor according to the present invention has the effects for inhibiting the proliferation of tumors in the living body by irradiating the ultrasound-sensitive substance with the low-intensity pulsed ultrasound waves resulting in inducing the acoustic cavitation phenomenon of the acoustic cavitation phenomenon-enhancing substance and consequently activating and enhancing the inhibitory effects of the ultrasound-sensitive substance.

As the ultrasound-sensitive substance to be used as an active component of the tumor proliferation inhibitor according to the present invention, there may be used any substance that can demonstrate the effect on the inhibition of tumor proliferation due to activation by the irradiation with low-intensity pulsed ultrasound waves. Specific examples may include, for example, a porphyrin derivative or a xanthene derivative.

Among the ultrasound-sensitive substances, the porphyrin derivative may include, for example, 7,12-bis(1-(2-(2-hydroxy-ethoxy) ethoxy)ethyl)-3,8,13,17-tetramethylporphyrin-2,18-dipro-pionato]manganese (DEG) as represented by formula [I]:

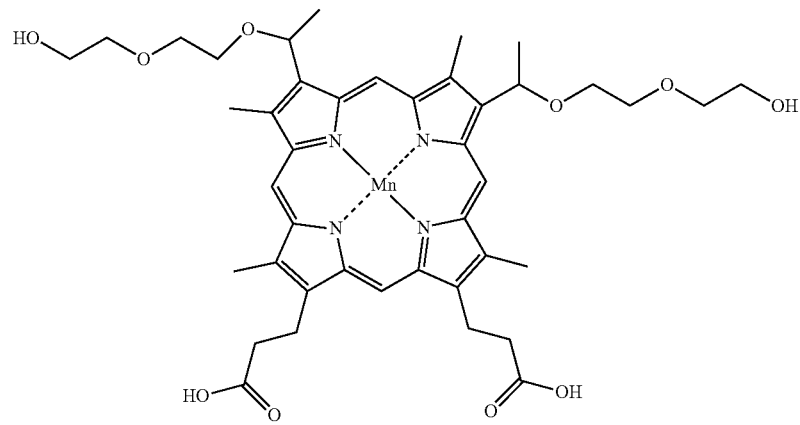

or 13,17-bis(1-carboxyethyl)-8-[2-(2,4-dichlorophenyl-hydra-zono) ethylidene]-3-ethenyl-7-hydroxy-2,7,12,18-tetramethyl-chlorin disodium salt as represented by formula [II]:

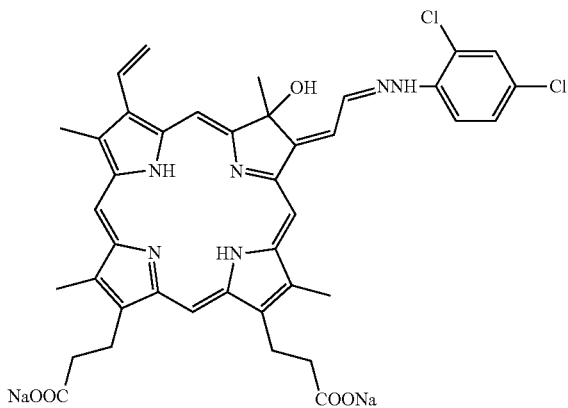

The ultrasound-sensitive substances to be used for the present invention means the substance that is substantially unreactive with a light, that is, that is little reactive or thoroughly unreactive with a light, but reactive with ultrasound waves.

The acoustic cavitation phenomenon-enhancing substance to be used for the present invention may include, for example, gas-filled nanobubbles such as nanobubbles or microbubbles. Specific examples are an ultrasound contrast agent containing lipid stabilized perfluorobutane microbubbles in an aqueous solution (SONAZOID™) and a microcrystalline suspension of galactose and palmitic acid which is shaken with sterile water prior to use to produce a milky suspension containing micrometer sized air bubbles (LEVOVIST™).

The low-intensity pulsed ultrasound waves to be used for the tumor proliferation inhibiting method according to the present invention are not limited to any particular one as long as they are so low in power that can activate the tumor proliferation inhibitor according to the present invention. It is preferred that they have power as low as approximately 0.1 to 10.0 W/cm$^2$ and 0.1 to 5.0 MHz. The MI value of the ultrasound waves may be preferably lower than 2. The recommended MI value for contrast radiography is from 0.2 to 0.3.

The tumor proliferation inhibitor according to the present invention may be formulated into preparations in accordance with ordinary formulating processes customarily applied in the art generally by admixing the ultrasound-sensitive substance and the acoustic cavitation phenomenon-enhancing substance with a preparation carrier in order to adapt the preparations to a type of administration. Although the type of administration of the preparations is not limited to a particular one, they may be administered orally or parenterally and in a dosage form appropriate for the type of administration. As the dosage form appropriate for oral administration, there may be mentioned oral preparations including, for example, tablets such as sugar-coated tablets or film-coated tablets, capsules, granules, emulsions, powders, suspensions, syrups and so on. As the dosage form appropriate for parenteral administration, there may be mentioned parenteral preparations including, for example, injections such as subcutaneous, intravenous, intramuscular and intraperitoneal injections and drops. The ultrasound-sensitive substance per se is not limited to a particular form and may be used in any form capable of being adapted to the type of administration of the preparations and, for example, in a powdery, particulate (containing nano-particulate) or liquid form.

As the preparation carriers to be used for the formulation of the tumor proliferation inhibitor according to the present invention, there may be mentioned, for example, excipients such as calcium carbonate, kaolin, sodium hydrogen carbonate, lactates, starches, crystalline cellulose, talc, granulated sugar, etc., binders such as dextrin, gums, alcoholized starches, gelatin, hydroxylpropyl cellulose, hydroxypropylmethyl cellulose, pullulan, etc., disintegrators such as carboxymethyl cellulose calcium, croscarmellose sodium, crospovidone, low substituted hydroxypropyl cellulose, partially alpha-carbohydrated starches, etc., lubricants such as magnesium stearate, calcium stearate, talc, starches, sodium benzoate, etc., colorants such as tar dyes, caramel, iron sesquioxide, titanium oxide, riboflavins, etc., sweeteners, flavors such as essences, etc., stabilizers such as sodium sulfite, etc., and preservatives such as parabens, sorbates, etc.

The tumor proliferation inhibitor according to the present invention may be administered in combination with other medicines, particularly anticancer drugs. As the way of administering the combined medicines, the tumor proliferation inhibitor may be administered in a form of preparations containing the other medicines or separately each other.

The dose of the tumor proliferation inhibitor according to the present invention may be appropriately varied depending upon a route of administration, a disease condition, an age and body weight of a patient, an amount or duration of ultrasonic irradiation or any other conditions. The dose of the tumor proliferation inhibitor is not limited to the particular one and may be appropriately varied in accordance with the kind of the tumor proliferation inhibitors as long as the effective concentration of the ultrasound-sensitive substance contained in the tumor proliferation inhibitor can be sustained in the living body at a sufficient amount during a period of time of ultrasonic irradiation.

In accordance with the present invention, the amount and period of time of irradiation with the low-intensity pulsed ultrasound waves may be appropriately varied depending upon a dose and a route of administration of the tumor proliferation inhibitor, a condition of disease, an age and body weight of a patient, and so on.

EXAMPLE 1

Figure 3:
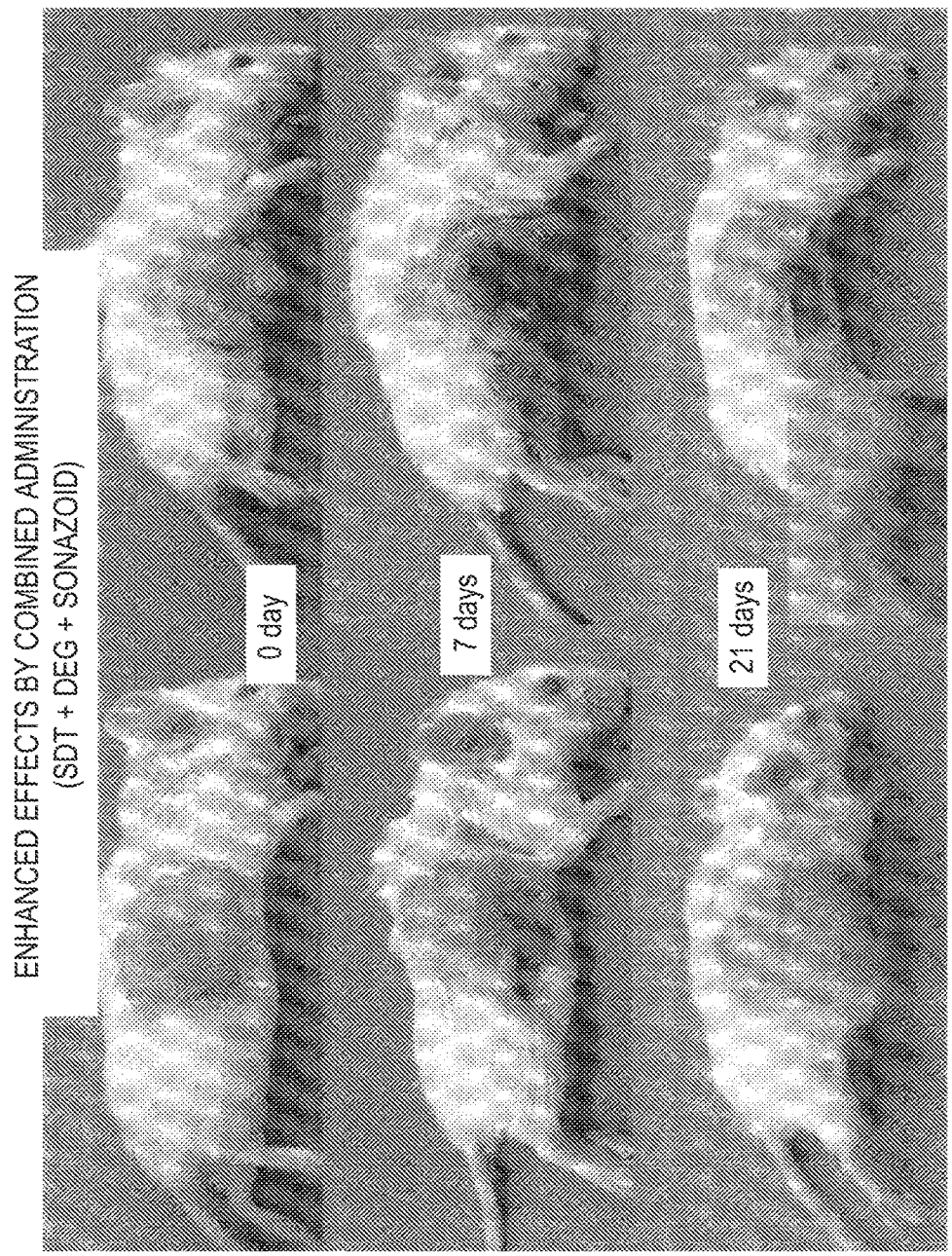
FIG. 3 is drawings showing the results of administration of DEG into tumors of mice with tumor immediately after treatment with ultrasound waves, one week and three weeks, respectively (Example 1).

SCID mice as cancer-carrying animals were inoculated subcutaneously with human gastric cancer cell line MKN-74 which was in turn grown to a diameter of the cancer size of approximately 20 mm and then subjected to treatment by ultrasound waves. The ultrasonic treatment was carried out using the porphyrin derivative, [7,12-bis(1-(2-(2-hydroxyethoxy)ethoxy)ethyl)-3,8,13,17-tetramethylporphyrin-2,18-dipropionato]manganese (DEG), as the ultrasound-sensitive substance and an ultrasound contrast agent containing lipid stabilized perfluorobutane microbubbles in an aqueous solution (SONAZOID™) as the acoustic cavitation phenomenon-enhancing substance by irradiating the mice with low-intensity pulsed ultrasound waves of 2 W/cm$^2$ and 1 MHz under a condition of 50% duty cycle for 10 minutes. The ultrasonic treatment was performed by suspending 5 μM of the ultrasound sensitive substance and 16 μL of the acoustic cavitation phenomenon-enhancing substance in 300 μL of saline and irradiating the mice with the ultrasound waves immediately after intratumoral administration of the resulting suspension. The states of development of the cancer were observed immediately after ultrasonic treatment, one week and three weeks thereafter. As a result, a dramatic regression of the cancer was recognized by the single treatment only in three weeks after the ultrasonic treatment. The results are shown in FIGS. 1 and 3.

COMPARATIVE EXAMPLE 1

Figure 2:
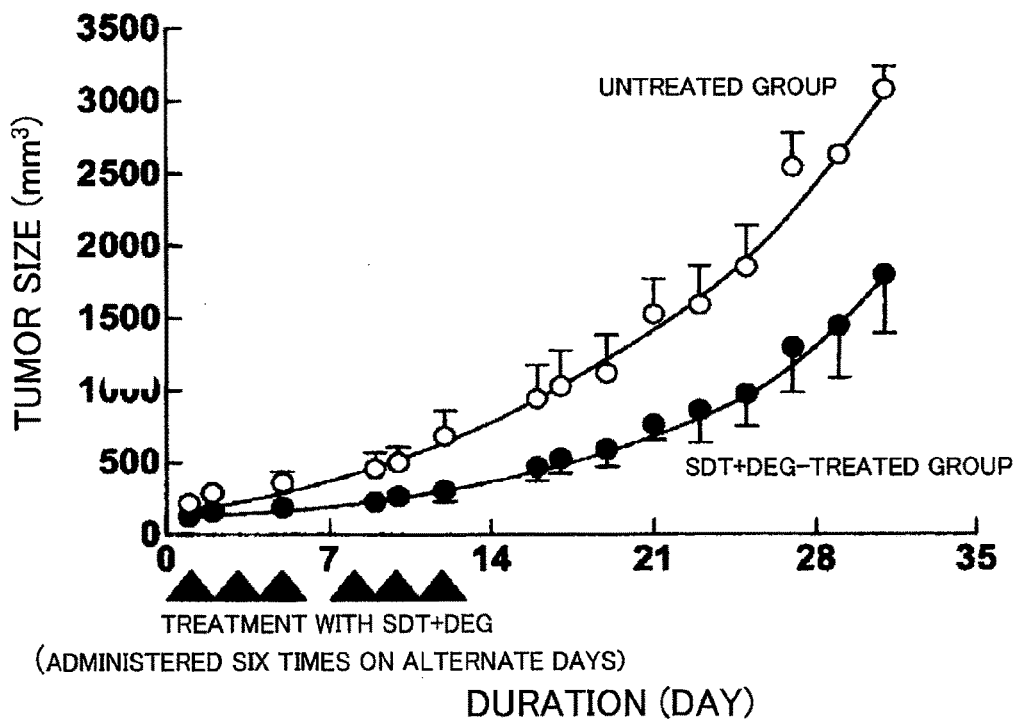
FIG. 2 is a graph showing the comparative effects of a single administration of DEG on tumor sizes when treated with low-intensity pulsed ultrasound waves after administration and when not treated thereafter (Comparative Example 1).

The ultrasonic treatment was carried out solely using DEG in substantially the same manner as in Example 1. The results are shown in FIG. 2.

EXAMPLE 2

Figure 4:
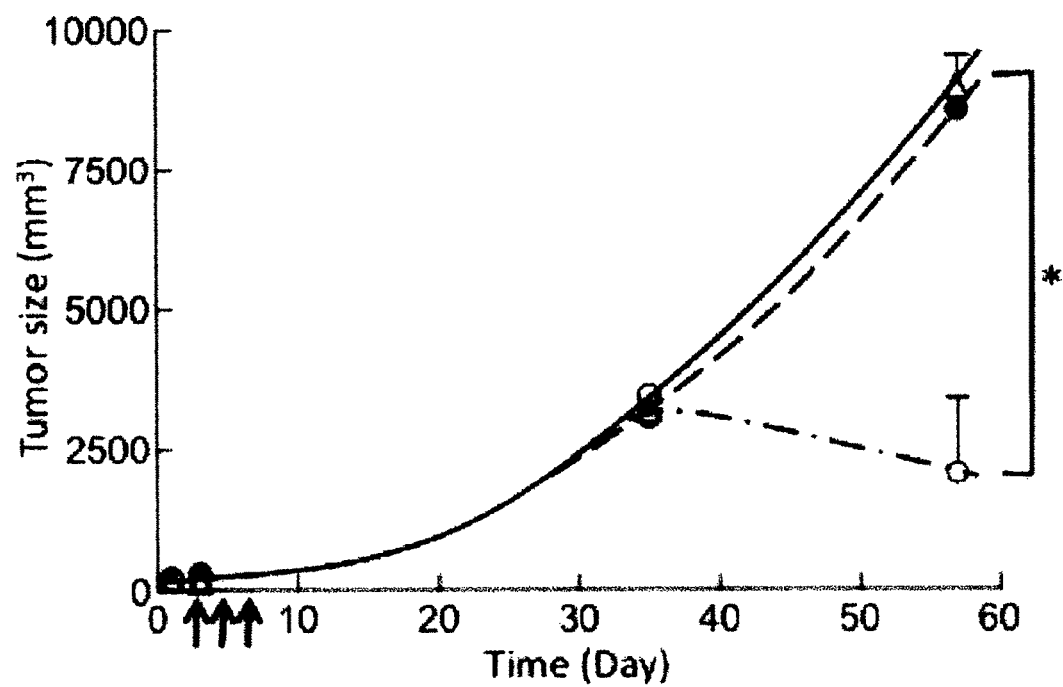
FIG. 4 is a graph showing the results of periodic measurements for tumor sizes at a particular site (subcutaneous tumor) of mice with tumor (Example 2).

This example reveals the inhibitory effect on cancer at a specific site (subcutaneous tumor). Mice were inoculated subcutaneously with ca. $5 \times 10^6$ cells of human gastric cancer cell line MKN-74 and a PBS suspension (200 μL) composed of the ultrasound-sensitive substance (DEG; 5 μM) and the acoustic cavitation phenomenon-enhancing substance (Szd; 16 μL) was administered intratumorally, followed by irradiating the mice with ultrasound waves of 1 W/cm$^2$ and 1 MHZ under a condition of 50% duty cycle for 10 minutes using Sonitron 100. The ultrasound waves were irradiated three times on alternate days. The results of the cancer sizes are shown by arrow mark (↑) in FIG. 4.

Figure 5:
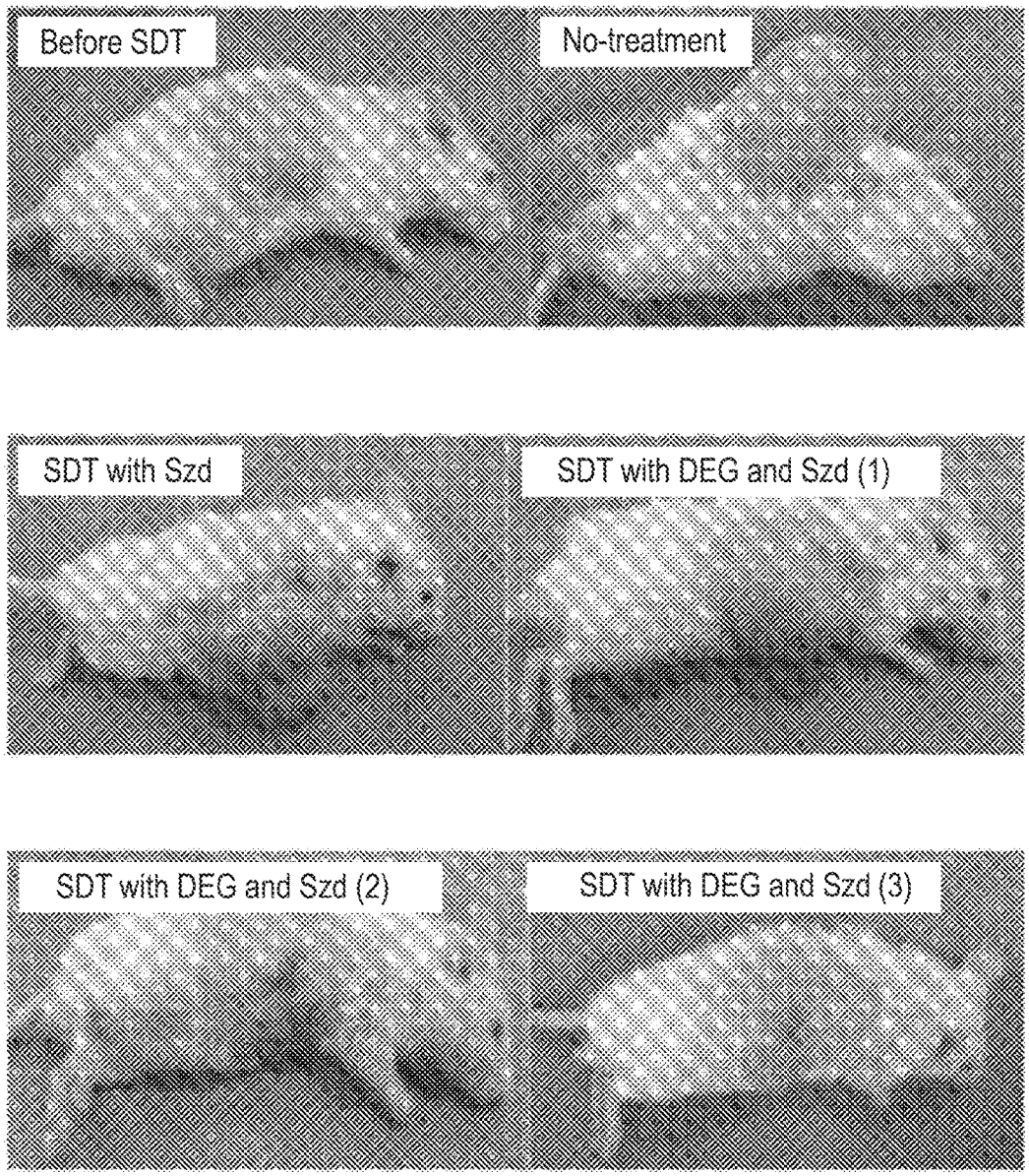
FIG. 5 is a graph showing the effect on inhibition of cancer at a particular site (subcutaneous tumor) of mice with tumor (Example 2).

As a result, no difference of the cancer sizes was recognized between the non-treated group (upper right figure of FIG. 5) and the SDT group with combined use of Szd (middle left figure of FIG. 5). In two cases (lower left and right figures of FIG. 5) out of three cases (middle right figure and lower left and right figures of FIG. 5) where DEG was used in combination with Szd showed remarkable effects, and even one remaining case showed a significant antitumor effect although its effect was not remarkable. These results reveal that the present invention was effective for subcutaneous tumor.

INDUSTRIAL APPLICABILITY

The present invention has the remarkable effects on an improvement in the quality of life of patients with cancers compared with photodynamic therapy using conventional photosensitive substances because the present invention can demonstrate highly antitumoral effects by using the ultrasound-sensitive substance and the acoustic cavitation phenomenon-enhancing substance in combination with ultrasound waves of a low intensity that has been applied for echo diagnosis.

The invention claimed is:

1. An in vivo method for activating an ultrasound-sensitive substance in tumor tissue for inhibiting the proliferation of a tumor, the method comprising the steps:
    administering an acoustic cavitation phenomenon-enhancing substance and a tumor proliferation inhibitor containing an ultrasound-sensitive substance substantially unreactive with light, but reactive with ultrasound waves to a subject with a tumor; and
    irradiating the subject to which the ultrasound-sensitive substance has been administered with low-intensity pulsed ultrasound waves which have a power of 0.1 to 10.0 W/cm$^2$ and 0.1 to 5.0 MHz to activate the ultrasound-sensitive substance,
    wherein said acoustic cavitation phenomenon-enhancing substance is an ultrasound contrast agent containing lipid stabilized perfluorobutane microbubbles in an aqueous solution,
    wherein the ultrasound-sensitive substance is [7,12-bis(1-(2-(2-hydroxy-ethoxy)ethoxy)ethyl)-3,8,13,17-tetramethylporphyrin-2,18-dipropionato]manganese (DEG) as represented by formula I:

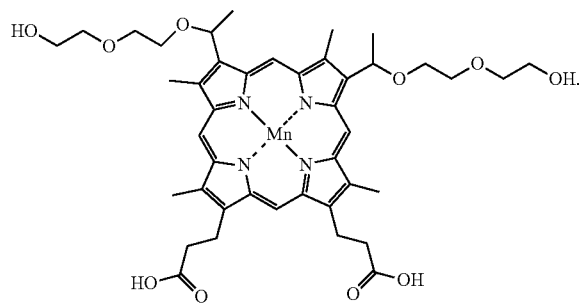

* * * * *